(12) United States Patent
Teng et al.

(10) Patent No.: US 10,526,668 B2
(45) Date of Patent: Jan. 7, 2020

(54) STREPTOMYCES AND METHOD FOR PRODUCING MILBEMYCIN A4 USING SAME

(71) Applicant: Zhejiang Hisun Pharmaceutical Co., Ltd., Taizhou (CN)

(72) Inventors: Yun Teng, Taizhou (CN); Meidong Xu, Taizhou (CN); Meiyi Mo, Taizhou (CN); Zhihui He, Taizhou (CN); Zhengjie Chen, Taizhou (CN); Lianiqing Jiang, Taizhou (CN); Hua Bai, Taizhou (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 32 days.

(21) Appl. No.: 15/562,187

(22) PCT Filed: Mar. 25, 2016

(86) PCT No.: PCT/CN2016/077355
§ 371 (c)(1),
(2) Date: Sep. 27, 2017

(87) PCT Pub. No.: WO2016/155567
PCT Pub. Date: Oct. 6, 2016

(65) Prior Publication Data
US 2019/0048427 A1    Feb. 14, 2019

(30) Foreign Application Priority Data
Mar. 27, 2015  (CN) .......................... 2015 1 0137374

(51) Int. Cl.
| | |
|---|---|
| *C12P 17/18* | (2006.01) |
| *C12P 17/10* | (2006.01) |
| *C12P 15/00* | (2006.01) |
| *C12R 1/55* | (2006.01) |
| *C12N 1/20* | (2006.01) |
| *C12N 15/76* | (2006.01) |

(52) U.S. Cl.
CPC ............... *C12R 1/55* (2013.01); *C12P 17/18* (2013.01); *C12N 1/20* (2013.01); *C12N 15/76* (2013.01)

(58) Field of Classification Search
CPC .......... C12N 1/20; C12P 17/181; C12P 17/18; C12R 1/55
USPC .............................. 435/253.3, 119, 440, 886
See application file for complete search history.

(56) References Cited

U.S. PATENT DOCUMENTS 3,950,360 A    4/1976  Aoki et al.

FOREIGN PATENT DOCUMENTS

| CN | 0274871 A1 | 7/1988 |
| CN | 101100651 A | 1/2008 |
| CN | 103468625 A | 12/2013 |
| CN | 103789339 A | 5/2014 |
| JP | H0889272 A | 4/1996 |

OTHER PUBLICATIONS

Hai-Yan Wang et al., "Combined application of plasma mutagenesis and gene engineering leads to 5-oxomilbemycins A3/A4 as main components from Streptomyces bingchenggensis," Appl Microbiol Biotechnol, Aug. 2, 2014 (Aug. 2, 2014), vol. 98, pp. 9703-9712.
Xiang-Jing Wang et al., "Role of nsdA in negative regulation of antibiotic production and morphological differentiation in Streptomyces bingchengensis," The Journal of Antibiotics, May 15, 2009 (May 15, 2009), vol. 52, No. 6, pp. 309-313, XP055499100.
Supplementary European Search Report for Application No. EP 16771322.1 dated Aug. 21, 2018.
Chinese Search Report for CN2015101373742 dated Jan. 2, 2019.
International Search Report for Application No. PCT/CN2016/077355, dated Jun. 29, 2016.
Chen, X. et al., Advances on Biological Pesticide Milbemycins, Pesticides, Apr. 2003, pp. 5-9, vol. 42, No. 4 (English translation of Abstract on p. 9).
Takiguchi, Y. et al., Milbemycins*, A New Family of Macrolide Antibiotics: Fermentation, Isolation and Physico-Chemical Properties, The Journal of Antibiotics, Oct. 1980, pp. 1120-1127, vol. 33, No. 10.
Nonaka, K. et al, Fermentative Production of Milbemycin a11 and a14: Appearance of Morphological Mutants During Large-Scale Fermentation, Actinomycetologica, Jan. 1999, pp. 1332-1341, vol. 13, No. 1.
Baoxin, Z. et al., Optimization of Fermentation Medium for Enhanced Production of Millbemycin by a Mutant of Streptomyces Bingchenggensis BC-X-1 Using Response Surface Methodology, African Journal of Biotechnology, Jul. 2011, pp. 7225-7235, vol. 10, No. 37.

*Primary Examiner* — Robert B Mondesi
*Assistant Examiner* — Mohammad Y Meah
(74) *Attorney, Agent, or Firm* — Lerner, David, Littenberg, Krumholz & Mentlik, LLP

(57) ABSTRACT

Provided are a *Streptomyces* (*Streptomyces hygroscopicus*) HS7522 and a method for preparing milbemycin A4 by culturing the *Streptomyces*. The *Streptomyces* (*Streptomyces hygroscopicus*) HS7522 of the present invention is deposited in "China General Microbiological Culture Collection Center" with an accession number of CGMCC No. 9671 on Sep. 16, 2014.

10 Claims, 3 Drawing Sheets
Specification includes a Sequence Listing.

STREPTOMYCES AND METHOD FOR PRODUCING MILBEMYCIN A4 USING SAME

CROSS-REFERENCE TO RELATED APPLICATIONS

The present application is a national phase entry under 35 U.S.C. § 371 of International Application No. PCT/CN2016/077355 filed Mar. 25, 2016, published as WO 2016/155567 A1, which claims priority from Chinese Patent Application No. 201510137374.2 filed Mar. 27, 2015, all of which are incorporated herein by reference.

TECHNICAL FIELD

The present invention relates to a new *streptomyces* and a method for producing milbemycin A4 by the fermentation culture of the *streptomyces*.

BACKGROUND ART

Milbemycin is natural product from microbial source, which can be used as pesticide, and there have been data showing that it is one of the best acaricides in the modern world. The US Environmental Protection Agency identifies it as a low-risk pesticide and Holland approves it as "GNO" (natural product in the production of crops). It belongs to ecology friendly pesticide and is applicable to the comprehensive prevention and control of organic agriculture pests and diseases, which has become a popular insecticidal and acaricidal agent in developed countries.

Milbemycin is a metabolite having insecticidal activity, which was screened from the fermentation broth of microorganism by Sankyo Company Limited of Japan using two-spotted spider mites as test insects (U.S. Pat. No. 3,950,360). After extensive fundamental researches, the mixture of the components of milbemycin A3 and milbemycin A4 (A3:A4=3:7) was used as an acaricide in 1983. The structures of milbemycin A3 and milbemycin A4 are as shown in formula I. In 1990, 1% of milbemycin emulsifiable concentrate (milbeknock) was used as an acaricide for tea and eggplants in Japan. In 1993, 1% of milbemycin emulsifiable concentrate was also registered in Japan as a pesticide for pears, peaches, watermelons, strawberries, eggplants and flowers. Currently, milbemycin has been registered in many countries, such as Japan and many countries in Europe and America, etc. and is recommended by the US Environmental Protection Agency to be used as a safe, environment friendly insecticidal and acaricidal agent.

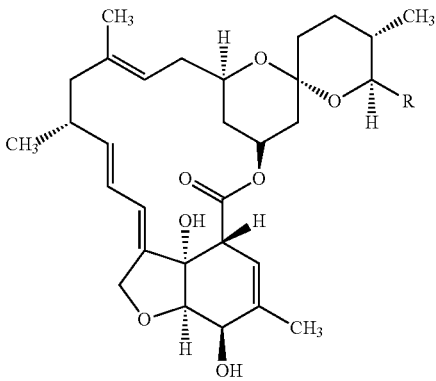

Milbemycin $A_3$: R = —$CH_3$
Milbemycin $A_4$: R = —$CH_2CH_3$

Formula I. The structures of milbemycin A3 and milbemycin A4.

Sankyo Company Limited of Japan is the original factory of milbemycin and its literature published in 1980 showed that the content of milbemycin A3+ milbemycin A4 was only about 150 mg/L (Yo Takiguchi et al, The J. of Antibiotics, 1980, October, 1120-1127). After mutagenesis of strain and optimization of fermentation conditions, in 1990, the content of milbemycin A3+ milbemycin A4 reached 530 mg/L (Koicchi Nonaka et al, Actinomycetol. 1990, 13:32-41). The domestic research of milbemycin started later, mainly concentrated in XIANG Wensheng research group of Northeast Agricultural University, and has also made a great breakthrough currently. For example, the unit content of milbemycin A3+ milbemycin A4 reached a maximum of 1595 mg/L in the literature published in 2011 (Zhang Baoxin et al, African J Biotechnol 10(37):7225-7235), and the unit content of milbemycin A3+ milbemycin A4 increased to 2237 mg/L in the Chinese patent CN 103468625 A.

The fermentation broth containing milbemycin has complex composition, wherein milbemycin A3 and milbemycin A4 are main components and other structural analogues are further comprised. In general, the ratio of milbemycin A3 to milbemycin A4 in the fermentation broth containing milbemycin is about 1:2, so the existing commercial product is also a mixture of components of A3 and A4. The main reason leading to this result is that it is difficult to separate A3 and A4 single component from the fermentation broth with similar proportions of A3 and A4, which affects the final yield. Achieving the single component production of A4 can further facilitate the application of milbemycin A4 single component in other fields. The most effective way to obtain a single component is to obtain a new strain capable of producing the single component and to further increase the fermentation unit.

SUMMARY OF INVENTION

In view of the above, an object of the present invention is to provide a microbial strain capable of increasing the unit yield of milbemycin A4, which is characterized in that the content of milbemycin A4 in its fermentation broth accounts for a percentage of more than 80% of the total content of A3 and A4 and the unit yield of milbemycin A4 can reach greater than 4000 ug/ml, the unit yield of milbemycin A3+ milbemycin A4 can reach greater than 5000 ug/ml, and the fermentation unit is high and the impurity content is low.

The microbial strain of *Streptomyces* HS7522 of the present invention was deposited on Sep. 16, 2014 at China General Microbiological Culture Collection Center (Address: Institute of Microbiology, Chinese Academy of Sciences, No. 1 Beichen West Road, Chaoyang District, Beijing) with an accession number of CGMCC No. 9671, classified and nominated as *Streptomyces hygroscopicus*, registered and proved to be survival. An application for converting the original deposit to a Budapest Treaty Deposit was received on Apr. 23, 2015. Notice of receipt of such application and viability of the deposit was received by Applicant on Sep. 10, 2015. There are no restrictions on the general public from accessing this deposit. Viability will be maintained for the duration of the patent term or for a period of twenty years. The main biological characteristics of *Streptomyces* HS7522 of the present invention are as follows: the colonies on ISP1 medium are white, on ISP2 medium pebble grey and on ISP3 medium are bright ivory; rounded, slightly raised in the middle, rugose and medium size of diameter (about 6 mm or so); except for on ISP1 medium, the spores abundant, substrate mycelia developed, mycelia are closely combined with medium and not easy to provoke; no pigment is produced on ISP1 and ISP2 media and khaki grey pigment is produced on ISP3 medium.

The present invention describes the characteristics of *Streptomyces* HS7522 on morphology and molecular levels. It can be confirmed that *Streptomyces* HS7522 belongs to *Streptomyces hygroscopicus* by comparing with known milbemycin-producing bacteria on the morphology and molecular levels. *Streptomyces* HS7522 has 99.5% homology with *Streptomyces* sp. NRRL 5739 16s rRNA and 99.9% homology with *Streptomyces bingchenggensis* BCW-1. The biggest difference between this strain and most of the milbemycin-producing bacteria in morphology is that the colonies of other strains, such as *Streptomyces* sp. CGMCC No. 7677, will secrete golden tears on the colony surface on the production plate, however, HS7522 on the same medium is stale grey and has no tears on the surface (see FIG. 2).

The present invention further provides a method for preparing milbemycin by using *Streptomyces* HS7522 (CGMCC No. 9671). The method comprises the process of aerobic fermentation of *Streptomyces* HS7522 (CGMCC No. 9671) in nutrient medium containing assimilable carbon source and assimilable nitrogen source.

In a preferred embodiment, the above assimilable carbon source is preferably selected from one of starch, dextrin, glucose, industrial molasses, glycerol, sucrose, lactose, maltose, trehalose, xylan, mannitol and sorbitol or a combination of the above substances.

In a preferred embodiment, the above assimilable nitrogen source is preferably selected from one of yeast extract, yeast powder, beef extract, tryptone, peptone, skim milk powder, whole milk powder, soybean cake powder, cottonseed cake powder, peanut cake powder, gluten powder, corn pulp dry powder, bran, urea and ammonium salt or a combination of the above substances.

In a preferred embodiment, the nutrient medium contains 2-12 g/L yeast extract, yeast extract paste or peptone, 20-200 g/L sucrose or molasses, 2-11 g/L skim milk powder or corn pulp, 5-11 g/L soybean cake powder, 5-15 g/L cottonseed cake powder or gluten powder, 0.2-1 g/L $K_2HPO_4$, 0.05-0.1 g/L $FeSO_4 \cdot 7H_2O$, 0.005-0.02 g/L $ZnSO_4$, 1-5 g/L $CaCO_3$, 0.01-0.05 g/L $CuSO_4$ and/or 0.1-0.5 g/L $Na_2MoO_4$.

In a preferred embodiment, the temperature of the fermentation culture is preferably 20-40° C., preferably 25-35° C., the pH of the medium is 6.0-8.0, preferably about 7.0; the culture time is 300-360 h; the dissolved oxygen is not less than 35%; the ventilation volume is 0.5-1.0 vvm.

The fermentation mode is submerged fermentation.
Milbemycin can be detected by the following HPLC method:
4.5 ml 75% ethanol is added into 0.5 ml fermentation broth. The resulting mixture is homogenously mixed and centrifuged at 3000 rpm for 15 min. The supernatant is taken for sample injection.
HPLC column: Zorbex RX-C8; 150 mm*4.6 mm; 5 μm
UV absorption wavelength: 240 nm
Temperature control: 22° C.
HPLC mobile phase conditions: as shown in Table 9
Injection volume: 10 μl.

The milbemycin-producing strain adopted in the present invention is *Streptomyces* HS7522 (CGMCC No. 9671), a spontaneous mutant or a mutant obtained by conventional mutagenesis of *Streptomyces* HS7522 (CGMCC No. 9671).

The main advantages of the present invention lie in:
1. The present invention provides a new milbemycin-producing strain *Streptomyces* HS7522 and a method for preparing milbemycin using same. *Streptomyces* HS7522 of the present invention is characterized in that the content of milbemycin A4 in its fermentation broth accounts for a percentage of more than 80% of the total content of A3 and A4, and the unit yield of milbemycin A4 can reach more than 4000 ug/ml, the unit yield of milbemycin A3+ milbemycin A4 can reach more than 5000 ug/ml, fermentation unit is high and the impurity content is low.
2. Since the *Streptomyces* HS7522 according to the present invention improves the proportion of milbemycin A4 in the fermentation product by the fermentation method, the difficulty of preparing the milbemycin A4 single component is reduced, which is advantageous for reducing the production cost and enlarging the application range of the milbemycin A4 single component.
3. The milbemycin A4 fermentation unit is improved. The titer of milbemycin A4 produced by *Streptomyces* HS7522 according to the present invention greatly increases compared with that of the original strain *Streptomyces milbemycinicus* CGMCC No. 7677, which is advantageous for industrial production.

DESCRIPTION OF EMBODIMENTS

Figure 1:
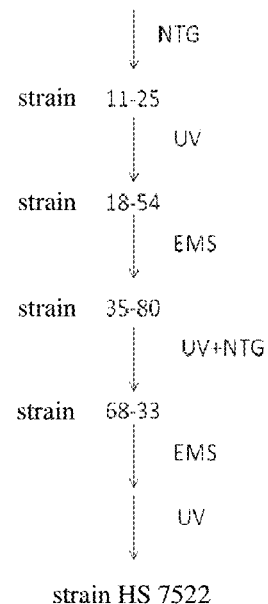
FIG. 1: The breeding diagram of *Streptomyces* HS7522 of the present invention.

The experimental methods used in the following examples are all conventional methods, unless otherwise specified.

The materials, reagents and the like used in the following examples are all commercially available, unless otherwise specified.

The present invention will now be further illustrated with reference to the following specific embodiments. It is to be understood that the following examples are intended to illustrate the present invention rather than limit the scope of the present invention.

Preparations of milbemycin A3 and milbemycin A4 standards are described in Example 1 of U.S. Pat. No. 3,950,360.

Sucrose is the product of Guangxi Dongmen Nanhua Sugar Industry Co., Ltd.

Yeast extract is the product of Zhejiang Dongcheng Pharmaceutical Co., Ltd.

Yeast extract paste is the product of Hefei Laisi Biological Engineering Co., Ltd.

Peptone is the product of Huzhou Confluence Biological science and technology Co., Ltd.

Molasses is the product of Guangdong Jiangmen Biological science and technology Co., Ltd.

Skim milk powder is the product of Hulunbeier Sanyuan Milk Co., Ltd.

Corn pulp is the product of Shandong Shouguang Juneng Golden Corn Co., Ltd.

Soybean cake powder is the product of Ningbo Beilun Jiangnan Oil Co., Ltd.

Cottonseed cake powder is the product of Beijing Kang Mingwei Medium Technology Co., Ltd.

Gluten powder is the product of Beijing Kang Mingwei Medium Technology Co., Ltd.

Example 1 Source of Strain

The *Streptomyces hygroscopicus* HS7522 of the present invention is a strain with high proportion of milbemycin A4, which is obtained by multiple rounds of mutagenesis and selective breeding (including the mutagenic means, such as NTG, EMS, UV, etc.) based on the milbemycin producing strain *Streptomyces milbemycinicus* CGMCC No. 7677 (see the Chinese Patent CN103789339A) which was deposited by the applicant of the present application. Compared with the original strain, the appearance of the strain has changed greatly, which belongs to morphological mutant.

*Streptomyces milbemycinicus* CGMCC No. 7677 strain was cultured on ISP3 slant medium at 28° C. for 10-12 d. Next, its mycelia were scraped under sterile conditions with an inoculating shovel, ground in a ground mouth tube and then suspended in sterile water to obtain bacterial suspension. The bacterial suspension was subjected to mutagenesis using NTG (nitrosoguanidine), EMS (ethylmethane sulfonate), UV (ultraviolet).

10 mg of NTG crystals was taken and dissolved in 10 ml of sterile Tris buffer (pH 8.0), and then 1 ml of the bacterial suspension was added using a transfer pipette. Then the resulting mixture was placed in medium at 28° C. in a rotary or reciprocating shaker for 30 min. The treated mixture was coated on ISP3 plate after appropriate dilution. The bacterial suspension which did not subject to mutagenesis treatment was also appropriately diluted and then coated on ISP3 plate as a control. After cultivation at 28 C for 10 d, the number of colonies was checked and the fatality rate was calculated.

5 ml-10 ml of single-cell bacterial suspension with $10^{-1}$ or $10^{-2}$ gradient was added to a plate (diameter of 9 cm) equipped with a clip. Then, the plate was placed in UV induction box and on a magnetic stirrer. Thereafter, open the lid and the plate was irradiated at UV15W at a distance of 30 cm for several minutes (usually 2-5 min) while stirring. After irradiation, the plate was wrapped with black cloth and then diluted for $10^2$-$10^7$ times with physiological saline (0.9% sodium chloride solution) and the dilutions were coated on ISP3 plates respectively to obtain mutagenesis groups.

1 ml of EMS was taken and dissolved in 2 ml of absolute ethyl alcohol and 22 ml of 0.1 mol/L phosphate buffer (pH 7.2) was further added. 5 ml of single-cell bacterial suspension with $10^{-1}$ or $10^{-2}$ gradient was added to a plate equipped with a clip. 5 ml of 4.0% EMS solution was then added into the plate and the final concentration of EMS solution was 2.0%. Then, the plate was placed on the magnetic stirrer and stirred for 20-60 min. 10 ml of 5% sodium thiosulfate was added into the mutagenesis plate to stop the reaction. The resulting mixture was then diluted for $10^2$-$10^7$ times with physiological saline in turn and the dilutions were coated on ISP3 plates respectively to obtain mutagenesis groups.

After multiple rounds of the above-mentioned single or combined mutagenesis, not less than 10,000 single colonies were selected and subjected to shake flask fermentation. The yield of milbemycin is detected by HPLC. The mutant *Streptomyces hygroscopicus* HS7522 was selected by multiple rounds of mutagenesis as shown in FIG. 1.

Example 2 Culture Characteristics of *Streptomyces* HS7522 Strain

The following experiments were conducted by reference to the relevant contents in "*Streptomyces* identification manual" ((《链霉菌鉴定手册》)), "The classification and identification of actinomycete" ((《放线菌的分类与鉴定》)) and "Common bacteria system identification manual" ((《常见细菌系统鉴定手册》)).

The colors and pigments of mycelia were observed after cultivation at 28° C. for 7-10 d on 10 kinds of media, i.e. ISP1, ISP2, ISP3, ISP4, ISP5, Gause's No. 1, calcium malate, nutrient agar, YMS and Czapek's (culture characteristics were shown in Table 1).

TABLE 1

Culture characteristics of *Streptomyces* HS7522 on 10 kinds of media

| Medium | Growth rate | Texture of colony | Colony surface color | Colony back color | Spore production | Soluble pigment |
|---|---|---|---|---|---|---|
| ISP1 | 11 mm | flat, petal-shaped on the edge, | white | brown beige | not abundant | / |

TABLE 1-continued

Culture characteristics of *Streptomyces* HS7522 on 10 kinds of media

| Medium | Growth rate | Texture of colony | Colony surface color | Colony back color | Spore production | Soluble pigment |
|---|---|---|---|---|---|---|
| ISP2 | 11 mm | wrinkled in the middle powdery, flat, cracked on the edge | pebble grey | beige red | slightly abundant | / |
| ISP3 | 12 mm | round, powdery, slightly heave in the middle | light ivory | khaki grey | abundant | khaki grey |
| ISP4 | 10 mm | flat, serrated on the edge | ivory | ivory | abundant | / |
| ISP5 | 11 mm | flat, highly serrated on the edge | white | light ivory | abundant | / |
| Gause's No. 1 | 10 mm | flat, halo on the edge | light gray close to white on the periphery, white in the middle | light gray close to white | not abundant | / |
| calcium malate | 7 mm | flat, serrated on the edge | white | light gray close to white | abundant | / |
| nutrient agar | 6 mm | flat, irregular cracks | white | beige | not abundant | / |
| YMS | 10 mm | powdery, flat cracked on the edge | papyrus white | green brown | abundant | / |
| Czapek's | 6 mm | flat, serrated on the edge | White in the middle, light gray close to white on the periphery | light gray close to white | not abundant | / |

Note:
"/" in Table 1 represents no pigment is produced.

Example 3 Physiological and Biochemical Tests

The following experiments are conducted by reference to the relevant contents in "*Streptomyces* identification manual" ((《链霉菌鉴定手册》)), "The classification and identification of actinomycete" ((《放线菌的分类与鉴定》)), "Common bacteria system identification manual" ((《常见细菌系统鉴定手册》)). Except for temperature tests, the cultivations were all carried out at 28° C. for 7-10 d.
1. Utilization of carbon sources: ISP9 was adopted as the basic medium and the final concentrations of various carbon sources were all 1.0%. Results were shown in Table 2.
2. Utilization of inorganic nitrogen sources: ISP9 was adopted as the basic medium, and both of the concentrations of $KNO_3$ and $(NH_4)_2SO_4$ were 0.1%. Results were shown in Table 2.
3. Degradation test and NaCl tolerance test (results were shown in Table 7) adopted GYEA (pH 6.8) as the basic medium. The concentrations of various degradation products were shown in Table 3. The results were shown in Table 3.
4. Oxidase and catalase tests (results were shown in Table 4), pH test (results were shown in Table 5) and temperature test (results were shown in Table 6) all adopted YMS medium.

TABLE 2

Utilizations of carbon sources and nitrogen sources of *Streptomyces* HS7522 strain

| Carbon source | Growth | Carbon source | Growth | Inorganic nitrogren source | Growth |
|---|---|---|---|---|---|
| D-glucose | 2 | salicin | 3 | $(NH_4)_2SO_4$ | + |
| D-raffinose | 3 | D-lactose | 2 | $KNO_3$ | − |
| D-xylose | 0 | galactose | 3 | | |
| D-sorbitol | 2 | inositol | 2 | | |
| L-arabinose | 0 | mannitol | 2 | | |
| glycerol | 3 | glycine | 0 | | |
| maltose | 3 | xylan | 3 | | |
| D-fructose | 1 | inulin | 2 | | |
| D-sucrose | 4 | rhamnose | 2 | | |

TABLE 3

Results of degradation test of *Streptomyces* HS7522 strain

| Degradation product | Concentration of degradation product | Result* | Degradation product | Concentration of degradation product | Result |
|---|---|---|---|---|---|
| adenine | 0.5% | 4, + | casein | 1.0% | 4, − |
| guanine | 0.5% | 4, − | tyrosine | 1.0% | 4, − |
| xanthine | 0.4% | 4, − | Tween-40 | 1.0% | 3, + |
| xylan | 0.4% | 4, − | Tween-60 | 1.0% | 3, + |
| hypoxanthine | 0.4% | 4, - | Tween-80 | 1.0% | 3, + |

TABLE 4

Main physiological and biochemical characteristics of
Streptomyces HS7522 strain

| Test | Result |
|---|---|
| gelatin liquefaction | + |
| amylohydrolysis | + |
| milk solidification | − |
| V.P test | − |
| milk peptonization | − |
| nitrate reduction | + |
| production of hydrogen sulfide | − |
| M.R test | − |
| utilization of cellulose | − |
| catalase | − |

TABLE 5 pH test of growth of Streptomyces HS7522 strain

| | pH | | | | | | | | |
|---|---|---|---|---|---|---|---|---|---|
| | 3.5 | 4.0 | 4.5 | 5.0 | 5.5 | 6.0 | 6.5 | 7.0 | 7.5 |
| Growth | 0 | 0 | 3 | 4 | 4 | 4 | 4 | 4 | 4 |

TABLE 6

Temperature test of growth of Streptomyces HS7522 strain

| | Temperature (° C.) | | | | |
|---|---|---|---|---|---|
| | 7 | 14 | 28 | 37 | 45 |
| Growth | 0 | 0 | 4 | 4 | 1 |

TABLE 7

Tolerance of Streptomyces HS7522 strain to NaCl

| | Concentration of NaCl | | | |
|---|---|---|---|---|
| | 1% | 4% | 7% | 10% |
| Growth of the strain | 2 | 0 | 0 | 0 |

Note:
in Tables 2-7, 0: no growth; 1: growth is weak; 2: can grow, with a small amount of spores; 3: good growth, with a large number of spores; 4: the best growth, with abundant spores; +: positive; −: negative.

Example 4: Sequence Analysis of 16S rDNA

The mycelia of the present invention grown well on ISP2 were collected and inoculated in TSB liquid medium containing glass beads, placed in an incubator at 28° C. and shake cultured at 250 r/min for 2-4 d. Then the mycelia were collected by centrifugation and washed twice with sterile water and then stored at 4° C. for use.
i. Mycelia were centrifuged at 1000 rpm for 1 min.
ii. Lysozyme solution (mycelia volume: lysozyme solution volume=1:5-10) was added till the final concentration of 3-4 mg/ml, then placed in water bath at 37° C. for 1-3 hr.
iii. 50-100 ug/ml proteinase K and 1% SDS were added, then placed in water bath at 37° C. for 0.5-3 h.
iv. Equal volume of neutral phenol/chloroform was added, shaked for 30 s, and then centrifuged at 12000 rpm for 5 min.
v. 1/10 volume of 3M NaAc solution and an equal volume of isopropanol were added into the supernatant and homogenously mixed, placed at room temperature for 5 min and then centrifuged at 12000 rpm for 5 min.
vi. The precipitate was washed twice with 70% ethanol, and dissolved in TE/RNase after drying.
vii. The extracted genome was used as a template and PCR amplification was then carried out using universal primers.

```
forward primer 27F is
5'-GAGAGTTTGATCCTGGCTCAG-3'    (SEQ ID No. 1)

Reverse primer 1495R is
5'-CTACGGCTACCTTGTTACGA-3'     (SEQ ID No. 2)
```

The reaction was carried out on a PCR cycler. The procedure was as follows: pre-denaturation at 95° C. for 5 min, 30 cycles of denaturation (94° C. for 45 s), annealing (55° C. for 45 s) and extension (72° C. for 90 s), then extension at 72° C. for 10 min. The reaction system is as follows:

| | |
|---|---|
| deionized water | 14.25 μL |
| 10 × PCR Buffer | 2.0 μL |
| dNTP mixture | 0.5 μL |
| Taq polymerase | 0.25 μL |
| Primer 1(27F) | 1.0 μL |
| Primer 2(1495R) | 1.0 μL |
| DNA template | 1.0 μL (quantified according to concentration) |

The PCR products were detected by 0.8% agarose gel electrophoresis. The products of clear bands were selected to be purified. The amplified products were recovered by gel electrophoresis and ligated to the T vector for sequencing. The sequence of the primary structure of 16S rDNA of the strain was obtained. The results showed that Streptomyces HS7522 had 99.5% homology with Streptomyces sp. NRRL 5739 16s rRNA and 99.9% homology with Streptomyces bingchenggensis BCW-1 by performing similarity search in the Genebank database (blast).

TABLE 8

Homologies between Streptomyces HS7522 and related strains

| Species name | GenBank No. | Number of different bases | Homology (%) |
|---|---|---|---|
| Streptomyces bingchenggensis BCW-1 strain BCW-1 | NR_074824.1 | 2 | 99.9 |
| Streptomyces sp. NRRL 5739 | EU170126 | 3 | 99.5 |
| Streptomyces sp. 1A01554 | EF012088.1 | 7 | 99.5 |
| Streptomyces sp. 172633 | HQ992750.1 | 8 | 99.5 |

Comparison of Streptomyces HS7522 with known milbemycin-producing bacteria

As reported by CN101100651A, the surface of colonies of milbemycin-producing bacteria Streptomyces bingchengsis sp. nov CGMCC No. 1734 on Gause's No. 1 medium was gray (black hygroscopic spots present), the back was yellow grey and yellow brown pigment was produced. Whereas the surface of colonies of Streptomyces HS7522 of the present invention on Gause's No. 1 medium was white, and the back was brown beige and no pigment was produced.

As reported by U.S. Pat. No. 3,950,360, the milbemycin-producing strain *Streptomyces* NRRL NO. 5739, its aerial mycelia on ISP2 medium were gray, the back was yellow brown, and there were many yellow tears on the colony surface and yellow pigment was produced; its aerial mycelia on ISP4 medium were gray, the back was khaki and there were also many yellow tears on the colony surface, bright olive green pigment was produced and arabinose and xylose could be utilized. Whereas the *Streptomyces* HS7522 of the present invention, its aerial mycelia on the SP2 medium were pebble grey, the back was beige red and there was no tear on the colony surface and no pigment was produced; its aerial mycelia on ISP4 medium were ivory, the back was ivory and there was no tear on the colony surface, no pigment was produced and arabinose and xylose cannot be utilized.

In summary, the *Streptomyces* HS7522 of the present invention belongs to genus *Streptomyces*, but it is different from the known milbemycin-producing strain *Streptomyces* NRRL NO. 5739 and *Streptomyces bingchengsis* sp. nov CGMCC No. 1734. *Streptomyces* HS7522 is a new strain.

Figure 2:
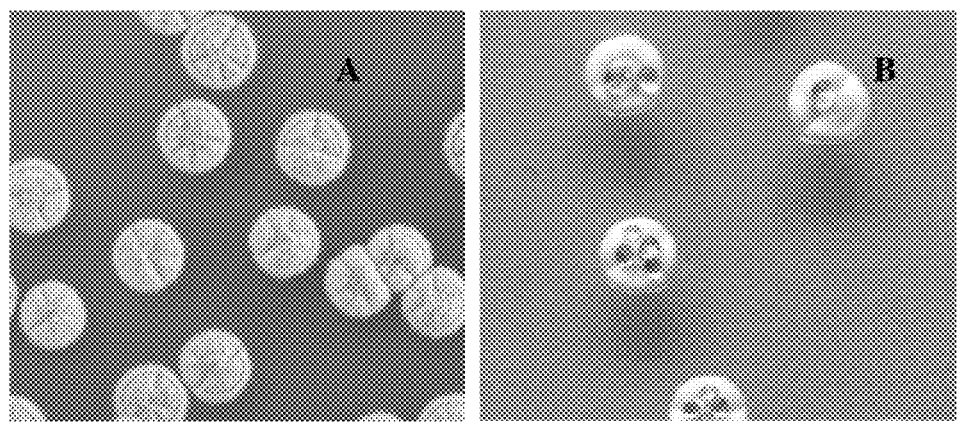
FIG. 2: The comparison chart of the colonial morphology of *Streptomyces* HS7522 strain of the present invention and that of *Streptomyces milbemycinicus* CGMCC No. 7677, wherein, B is the colonial morphology of *Streptomyces milbemycinicus* CGMCC No. 7677, and A is the colonial morphology of *Streptomyces* HS7522 of the present invention.

The comparison chart of colonial morphology of *Streptomyces* HS7522 strain of the present invention with that of the *Streptomyces milbemycinicus* CGMCC No. 7677 is shown in FIG. 2.

Example 5 Preparation of Milbemycin A4

1. Preparation of Mycelia on Slant and Culture

The formulation of slant spore medium (g/L): yeast extract 2, malt extract 2, sucrose 10, skim milk powder 1.2, agar 20, pH was 7.0-7.2 before sterilization. Test tube was 30×200 mm and filled volume was 20 mL. After sterilization at 121° C. for 20 min, the medium was cooled to 50-60° C. to form slant. The slant was then inoculated with a ring of mycelia. After cultivation at the temperature of 28±1° C. for 10 d, the mycelia were mature.

2. Preparation of Seed Medium and Culture

The formulation of seed medium (g/L): yeast extract 5, peptone 5, sucrose 20, skim milk powder 3, $K_2HPO_4$ 0.8, pH was 6.8-7.2 before sterilization. The filled volume of shaking flask was 250 mL and triangular flask 30 mL. The seed medium was sterilized at 121° C. for 20 min. The inoculation amount of the bacteria was $105\text{-}10^6$ c.f.u./mL, the culture temperature was 28±1° C., and shaking cultured at 250 rpm for 48 h in shaker.

3. Preparation of Milbemycin A4 Fermentation Medium and Culture

The formulation of fermentation medium (g/L): yeast extract 5, sucrose 100, skim milk powder 11, soybean cake powder 10, cottonseed cake powder 14, $K_2HPO_4$ 1, $FeSO_4 \cdot 7H_2O$ 0.1, $ZnSO_4$ 0.02, $CaCO_3$ 5, $CuSO_4$ 0.05, $Na_2MoO_4$ 0.5. The filled volume of shaking flask was 250 mL and triangular flask 30 mL. The fermentation medium was sterilized at 121° C. for 20 min and then inoculated with seed culture in an inoculation amount of 10% (volume percentage) and shaking cultured at the temperature of 28±1° C., 250 rpm for 14 d in shaker. After fermentation, the fermentation broth was detected by HPLC.

The HPLC detection method of milbemycin is as follows:
0.5 ml of fermentation broth was taken and 4.5 ml of 75% ethanol was then added and mixed homogenously. The resulting mixture was centrifuged at 3000 rpm for 15 min and the supernatant was taken for sample injection.
HPLC column: Zorbex RX-C8; 150 mm*4.6 mm; 5 μm
UV absorption wavelength: 240 nm
Temperature control: 22° C.

The conditions of HPLC mobile phase were as follows:

TABLE 9

Gradient Elution

| Flow rate (ml/min) | Time (min) | Acetonitrile | Methanol | Water |
|---|---|---|---|---|
| 1.0 | 0 | 50 | 24 | 26 |
| 1.0 | 6 | 50 | 24 | 26 |
| 1.0 | 10 | 53 | 24 | 23 |
| 1.0 | 12 | 53 | 24 | 23 |
| 1.0 | 15 | 60 | 20 | 20 |
| 1.0 | 16 | 60 | 20 | 20 |
| 1.0 | 17 | 100 | 0 | 0 |
| 2.0 | 18.5 | 100 | 0 | 0 |
| 2.0 | 18.6 | 50 | 24 | 26 |
| 1.0 | 21 | 50 | 24 | 26 |

Injection volume: 10 μl.

Figure 3:
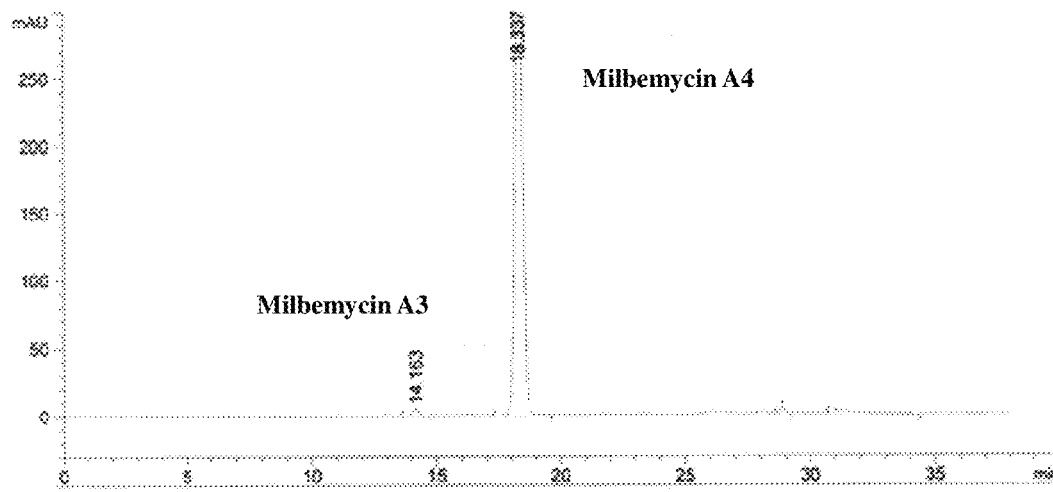
FIG. 3: HPLC chromatogram of milbemycin A3 standard and milbemycin A4 standard.

The HPLC chromatograms of the milbemycin A3 standard and milbemycin A4 standard under the same conditions were shown in FIG. 3 (the HPLC detections of the fermentation brothes of the following examples all included the HPLC detection steps of the milbemycin A3 standard and milbemycin A4 standard).

Figure 4:
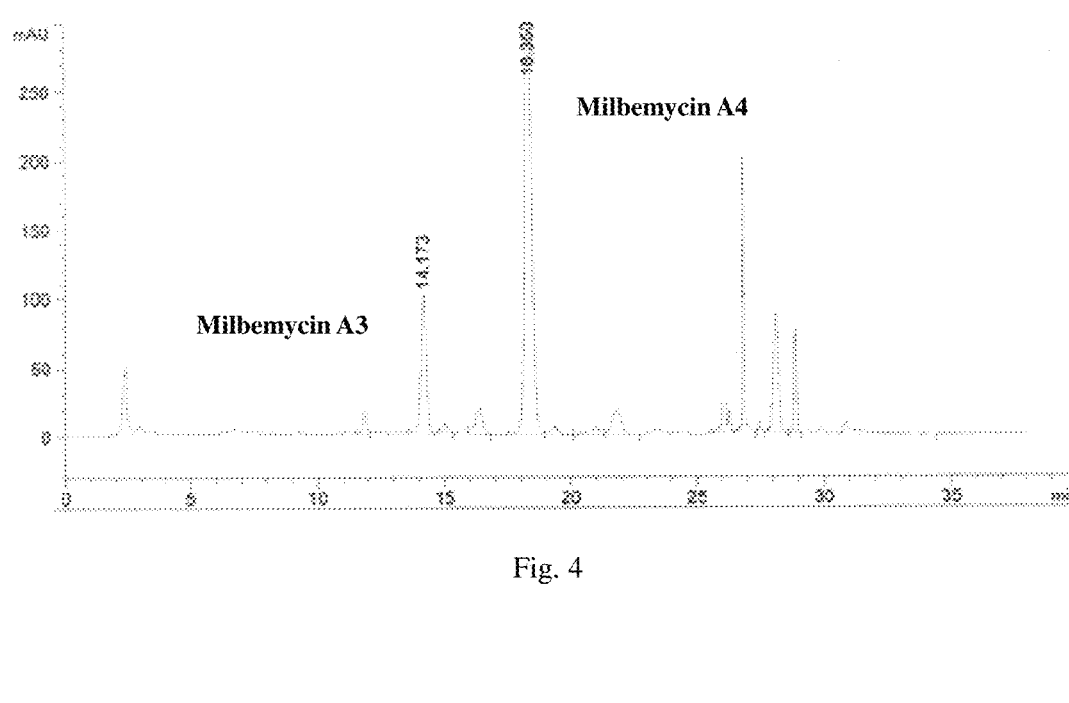
FIG. 4: HPLC chromatogram of the fermentation broth of Example 5. The content of milbemycin A4 is 3900 mg/L, the content of milbemycin A3 is 967 mg/L and the content of milbemycin A4 accounts for 80.1% of the total content of A3 and A4.

The HPLC chromatogram of the fermentation broth was shown in FIG. 4.

By comparison of the retention time of HPLC chromatograms of target products with that of milbemycin A3 standard and milbemycin A4 standard under the same conditions, the target products in the fermentation broth were determined to be milbemycin A3 and milbemycin A4 (the target products were determined to be milbemycin A3 and milbemycin A4 by comparison of HPLC chromatograms of the fermentation brothes of the following examples).

The content of milbemycin A4 in the fermentation broth was 3900 mg/L, the content of A3 was 967 mg/L, and the content of milbemycin A4 accounted for 80.1% of the total content of A3 and A4.

Example 6 Preparation of milbemycin A4

1. Preparation of Seed Culture in the Seeding Tank

10 L of seed medium (see Example 5 for the formulation of seed medium, meanwhile 0.25% of defoamer was added as antifoaming agent) was fed into 15 L seeding tank. Then steam sterilization was carried out at 121° C. for 30 min. After cooling, 200 ml of shake flask seed culture was inoculated therein and then cultured at the temperature of 28±1° C., stirring rate of 150 rpm and ventilation volume of 1 vvm for 48 h.

2. Preparation of Fermentor Medium and Culture

The formulation of fermentation medium was the same as that in Example 5, except that 0.25% of defoamer needed to be added as antifoaming agent. The volume of fermentor was 50 L and the volume of feed material was 35 L. The pH of the fermentation medium was 7.0-7.6 before sterilization. Steam sterilization was then carried out at 121° C. for 25 min. After cooling, about 3.5 L of seeding tank culture was inoculated therein and then fermented at the temperature of 28±1° C., stirring rake stirred with the lowest rate of 150 rpm depending on the dissolved oxygen, which was not less than 35%. The ventilation volume was 0.6 vvm for 14 d and then the fermentation broth in the fermentor was released. The fermentation broth was detected by HPLC as shown in Example 5, and in the fermentation broth, the content of milbemycin A4 was determined to be 4100 mg/L, the content of A3 was 962 mg/L, and the content of milbemycin A4 accounted for 81% of the total content of A3 and A4.

Figure 5:
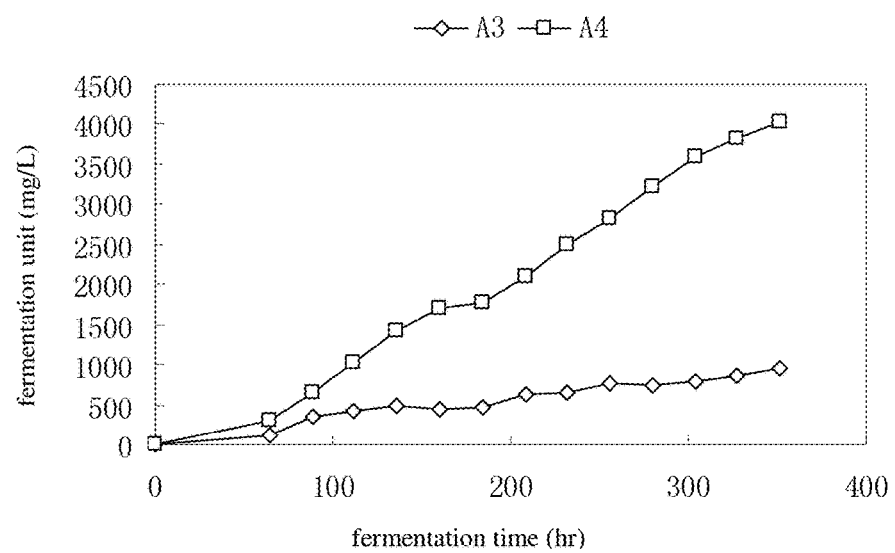
FIG. 5: The fermentation curves of *Streptomyces* HS7522 of the present invention in producing milbemycin A3 and milbemycin A4 in 50 L fermentor of Example 6.

The fermentation curves of milbemycin A3 and milbemycin A4 produced in the fermentor were shown in FIG. 5.

Figure 6:
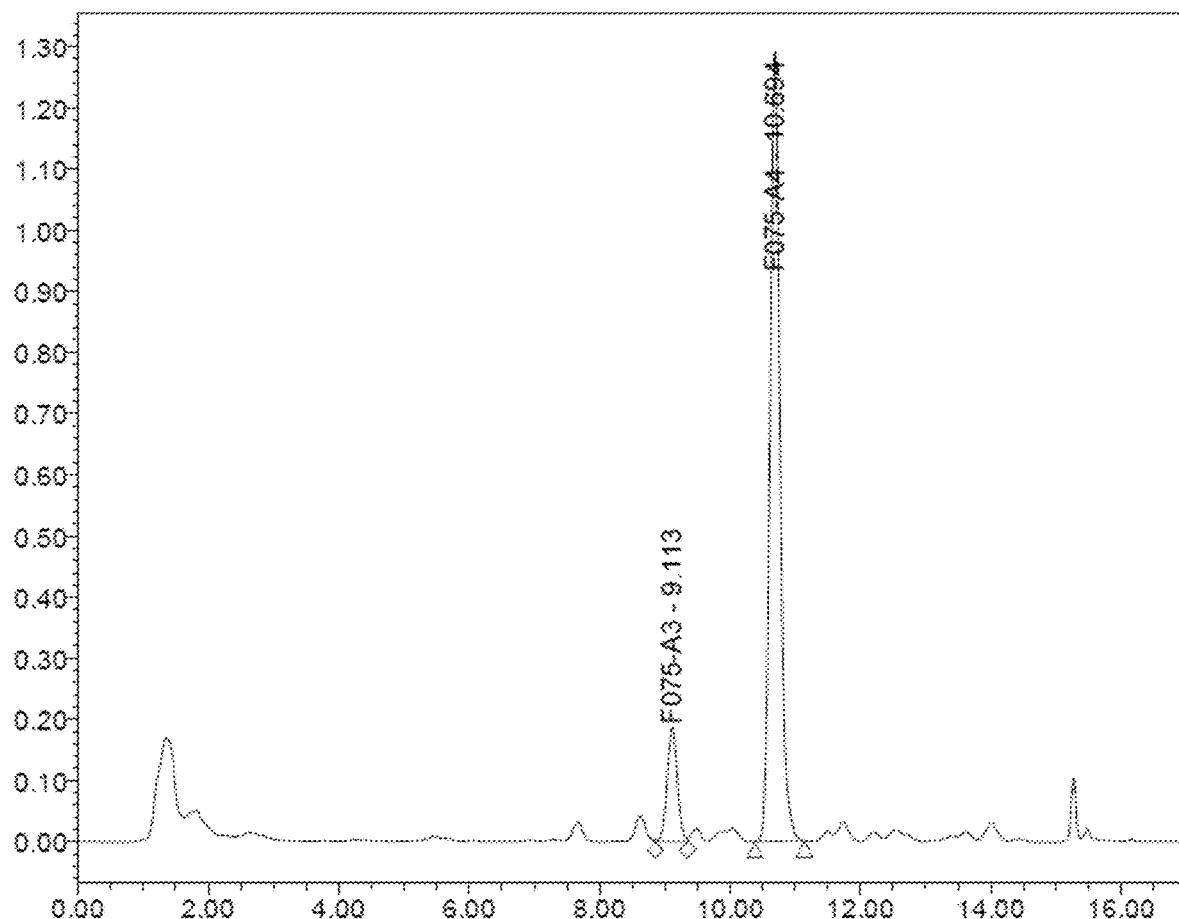
FIG. 6: HPLC chromatogram of milbemycin A4 produced by *Streptomyces* HS7522 of the present invention under the conditions of Example 6. The content of milbemycin A4 is 4100 mg/L, the content of milbemycin A3 is 962 mg/L and the content of milbemycin A4 accounts for 81% of the total content of A3 and A4.

The HPLC chromatogram of milbemycin A4 (F075-A4) in the fermentation broth was shown in FIG. 6.

Example 7 Preparation of Milbemycin A4

1. Preparation of Seed Culture in the Seeding Tank 8T of seed medium (see Example 5 for the formulation of seed medium, meanwhile 0.25% of defoamer was added as antifoaming agent) was fed into 15T seeding tank. Steam sterilization was carried out at 121° C. for 35 min. After the sterilization, the volume of the medium was 10T. After cooling, 2 L of shake flask seed culture was inoculated therein and then cultured at the temperature of 28±1° C., stirring rate of 100 rpm and ventilation volume of 0.8 vvm for 48 h.

2. Preparation of Fermentor Medium and Culture

The formulation of fermentation medium was the same as that in Example 5, except that 0.3% of defoamer was added as antifoaming agent. The fermentor was 70T and the volume of feed material was 55T. The pH was 6.8-7.6 before sterilization. Steam sterilization was carried out at 121° C. for 35 min. After cooling, about 6T of seeding tank culture was inoculated therein and then fermented at the temperature of 28±1° C., stirring rake stirred with the lowest rate of 50 rpm depending on the dissolved oxygen, which was not less than 35%. The ventilation volume was 0.5 vvm for 14 d and then the fermentation broth in the fermentor was released. The fermentation broth was detected by HPLC as shown in Example 5, and in the fermentation broth, the content of milbemycin A4 was determined to be 4020 mg/L, the content of A3 was 961 mg/L, the content of milbemycin A4 accounted for 80.7% of the total content of A3 and A4.

Example 8 Preparation of milbemycin A4

The formulation of seed medium (g/L): yeast extract powder 5, peptone 5, sucrose 40, $K_2HPO_4$ 0.5, pH was 7.0-7.4 before sterilization. The filled volume of shaking flask was 250 mL and triangular flask 25 mL. Then the seed medium was sterilized at 121° C. for 20 min. A piece of bacteria clump with an area of 1×2 cm was dug from the slant in Example 5 and inoculated into a seed bottle and cultured at 28±1° C. for 45 hr. 2.5 mL of the above seed culture was then inoculated into the fermentation medium (g/L): yeast extract paste 12, molasses 200, skim milk powder 11, soybean cake powder 11, cottonseed cake powder 11, $K_2HPO_4$ 1, $FeSO_4 \cdot 7H_2O$ 0.1, $ZnSO_4$ 0.02, $CaCO_3$ 5, $CuSO_4$ 0.05, $Na_2MoO_4$ 0.5. The filled volume of shaking flask was 250 mL and triangular flask 30 mL, which were sterilized at 121° C. for 20 min. The resulting mixture was shaking cultured at 28±1° C., 250 rpm in shaker for 14 d. After fermentation, the fermentation broth was determined by HPLC as shown in Example 5, and in the fermentation broth, the content of milbemycin A4 was determined to be 3960 mg/L, the content of A3 was 929 mg/L, the content of milbemycin A4 accounted for 81% of the total content of A3 and A4.

Example 9 Preparation of Milbemycin A4

Seed culture was prepared according to Example 8 and then 2.5 mL of seed culture was inoculated into the fermentation medium (g/L): peptone 10, sucrose 140, corn pulp 10, soybean cake powder 10, gluten powder 15, $K_2HPO_4$ 1, $FeSO_4 \cdot 7H_2O$ 0.1, $ZnSO_4$ 0.02, $CaCO_3$ 5, $CuSO_4$ 0.05, $Na_2MoO_4$ 0.5, with the filled volume of shaking flask 250 mL and triangular flask 30 mL, which were sterilized at 121° C. for 20 min. The resulting mixture was then shaking cultured at 28±1° C., 250 rpm in shaker for 14 d. After fermentation, the fermentation broth was determined by HPLC as shown in Example 5, and in the fermentation broth, the content of milbemycin A4 was determined to be 4100 mg/L, the content of A3 was 900 mg/L, the content of milbemycin A4 accounted for 82% of the total content of A3 and A4.

Comparative Example 1 Comparison of *Streptomyces* HS7522 of the Present Invention with the Original Strain CGMCC No. 7677 in Producing Milbemycin 1. Compositions of slant, seed medium and fermentation medium, and culture conditions were the same as that of Example 5, and the original strain CGMCC No. 7677 was used to carry out five groups of parallel fermentation. After fermentation, the fermentation brothes were detected by HPLC as shown in Example 5, and the average content of milbemycin A4 was determined to be 729 mg/L, the average content of A3 was 297 mg/L, the content of milbemycin A4 accounted for 71% of the total content of A3 and A4.

2. Compositions of slant, seed medium and fermentation medium, and culture conditions are the same as that of Example 5, and *Streptomyces* HS7522 of the present invention was used to carry out five groups of parallel fermentation. After fermentation, the fermentation brothes were detected by HPLC as shown in Example 5, and the average content of milbemycin A4 was determined to be 4016 mg/L, the average content of A3 was 942 mg/L, the content of milbemycin A4 accounted for 81% of the total content of A3 and A4.

4.

The invention claimed is:

1. A *Streptomyces hygroscopicus* HS7522, which is deposited with an accession number of CGMCC No. 9671 and has the ability to produce milbemycin.

2. A method of producing milbemycin, comprising the step of aerobic fermentation of *Streptomyces* HS7522, which is deposited with an accession number of CGMCC No. 9671, in a nutrient medium containing assimilable carbon source and assimilable nitrogen source.

3. The method according to claim 2, wherein the assimilable carbon source is selected from one of starch, dextrin, glucose, industrial molasses, glycerol, sucrose, lactose, maltose, trehalose, xylan, mannitol and sorbitol or a combination of the above substances.

4. The method according to claim 2, wherein the assimilable nitrogen source is selected from one of yeast extract, yeast powder, beef extract, tryptone, peptone, soybean cake powder, cottonseed cake powder, peanut cake powder, gluten powder, corn pulp dry powder, bran, urea and ammonium salt or a combination of the above substances.

5. The method according to claim 2, wherein the nutrient medium contains 2-12 g/L yeast extract, yeast extract paste or peptone, 20-200 g/L sucrose or molasses, 2-11 g/L skim milk powder or corn pulp, 5-11 g/L soybean cake powder, 5-15 g/L cottonseed cake powder or gluten powder, 0.2-1 g/L $K_2HPO_4$, 0.05-0.1 g/L $FeSO_4 \cdot 7H_2O$, 0.005-0.02 g/L $ZnSO_4$, 1-5 g/L $CaCO_3$, 0.01-0.05 g/L $CuSO_4$ and/or 0.1-0.5 g/L $Na_2MoO_4$.

6. The method according to claim 2, wherein the temperature of the fermentation is 20-40° C.; pH of the medium is 6.0-8.0; the fermentation time is 300-360 h.

7. The method according to claim 2, wherein the dissolved oxygen is not less than 35% during the fermentation.

8. The method according to claim 2, wherein the ventilation volume is 0.5-1.0 vvm during the fermentation.

9. The method according to claim 6, wherein the temperature of the fermentation is 25-35° C.

10. The method according to claim 6, wherein the pH of the medium is 7.0.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: artificial sequence
<220> FEATURE:
<221> NAME/KEY: primer_bind
<223> OTHER INFORMATION: forward universal primer 27F

<400> SEQUENCE: 1
gagagtttga tcctggctca g                                           21
```

```
<210> SEQ ID NO 2
<211> LENGTH: 20
<212> TYPE: DNA
<213> ORGANISM: artificial sequence
<220> FEATURE:
<221> NAME/KEY: primer_bind
<223> OTHER INFORMATION: reverse universal primer 1495R

<400> SEQUENCE: 2
ctacggctac cttgttacga                                           20
```